United States Patent

Büttner et al.

[11] 4,383,126
[45] May 10, 1983

[54] PREPARATION OF MONOALKYL ETHERS OF HYDROXYPHENOLS

[75] Inventors: Gerhard Büttner, Pulheim; Artur Judat, Langenfeld; Udo Allenbach, Cologne; Manfred Lenthe, Odenthal, all of Fed. Rep. of Germany

[73] Assignee: Bayer Aktiengesellschaft, Leverkusen, Fed. Rep. of Germany

[21] Appl. No.: 315,126

[22] Filed: Oct. 26, 1981

[30] Foreign Application Priority Data

Nov. 15, 1980 [DE] Fed. Rep. of Germany ....... 3043230

[51] Int. Cl.³ .............................................. C07C 41/16
[52] U.S. Cl. .................................... 568/650; 568/652
[58] Field of Search ................................ 568/650, 652

[56] References Cited

U.S. PATENT DOCUMENTS

| | | | |
|---|---|---|---|
| 1,888,827 | 11/1932 | Klarmann et al. | 568/650 X |
| 3,274,260 | 9/1966 | Levy et al. | 568/650 |
| 3,689,570 | 9/1972 | Gradeff et al. | 568/650 |
| 3,927,118 | 12/1975 | Ozretich | 568/650 X |

FOREIGN PATENT DOCUMENTS 2255279  7/1975  France .
2006211A  5/1979  United Kingdom .

OTHER PUBLICATIONS

Condensed Chemical Dictionary, (8th Ed.) (1981) 180.

Primary Examiner—Bernard Helfin
Attorney, Agent, or Firm—Sprung, Horn, Kramer & Woods

[57] ABSTRACT

A process for the preparation of a monoalkyl ether of a hydroxyphenol of the formula

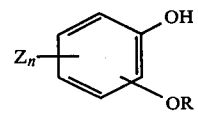

in which
Z each independently is hydrogen or a substituent which is stable under the reaction conditions,
R is lower alkyl, and
n is 1, 2, 3 or 4, comprising reacting a hydroxyphenol of the formula

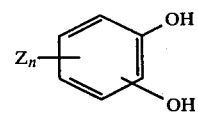

with an alkyl halide, alkyl sulphonate or aryl sulphonate alkylating agent of the formula

R—X in which X is a halogen atom, or an alkylsulphonyloxy or arylsulphonyloxy radical,
at a temperature from about 130° C. to 200° C. and in the presence of an alkali metal base or alkaline earth metal base and of a diluent comprising a polyhydroxyalkyl ether having at least one OH group. Advantageously the base is sodium carbonate, sodium bicarbonate, potassium carbonate or potassium bicarbonate, the hydroxyphenol is pyrocatechol, the alkylating agent is isopropyl chloride, isopropyl $C_{1-4}$-alkyl-1-sulphonate, isopropyl benzenesulphonate or isopropyl tolyenesulphonate, and the polyhydroxyalkyl ether is glycol monomethyl ether, about 1.5 to 1.8 mols of alkylating agent and about 1 to 2 mols of the base being employed per mol of pyrocatechol, about 1.5 to 2.5 parts by weight of the glycol monomethyl ether being employed per part by weight of pyrocatechol, the reaction being effected in an inert atmosphere under elevated pressure.

13 Claims, No Drawings

PREPARATION OF MONOALKYL ETHERS OF HYDROXYPHENOLS

The present invention relates to an unobvious process for the monoalkylation of hydroxyphenols.

A number of side-reactions can occur in the selective monoetherification of hydroxyphenols. The undesired diether formation significantly reduces the yield of monoether; in addition to this, variable amounts of nuclear alkylation products are obtained, depending on the solvent employed. If the diether formation is to be suppressed by only partial conversion of the hydroxyphenol in an economical procedure, the expensive hydroxyphenol must be recovered. In general, this is only possible by means of a troublesome extraction with large amounts of solvent. Because of the high boiling point of these compounds, a recovery of the hydroxyphenol employed by means of distillation leads on the one hand to substantial losses and on the other hand to hardly reusable hydroxyphenol, since the nuclear alkylation products formed have a similar boiling point to that of the hydroxyphenol.

Various processes have been proposed for the solution of these problems in the preparation of monoethers from hydroxyphenols. It is already known from DOS (German Published Specification) No. 2,007,737 that hydroxyphenols may be monoalkylated with lower alkyl halides, if a two-phase reaction is carried out, using an alkali metal carbonate as a base, in a water-immiscible solvent at temperatures up to 130° C. and with a reaction time of 8 to 10 hours. Tertiary amines can be used as catalysts. The optimum quantity of water is 3 to 4 moles of water per mole of hydroxyphenol.

In order to accelerate the reaction rate, quaternary ammonium or phosphonium compounds, which act as phase-transfer catalysts, are introduced instead of tertiary amines, according to a similar process (DOS No. 2,925,763).

In both processes, in spite of two-phase reaction and catalysts, a satisfactory selectivity for the monoether is only obtained if the conversion of hydroxyphenol is not complete (<70%). For an economical preparation of the monoether, the unreacted hydroxyphenol must be recovered from both phases, a process which requires a high outlay (since it is technically difficult) and which is associated with the problem described hereinabove at the outset.

Furthermore, a process for the selective monoalkylation of hydroxyphenols is described in DOS No. 2,451,936 (U.S. Pat. No. 3,927,118). In this process, hydroxyphenols are reacted in dipolar aprotic solvents with alkylating agents and using an alkaline earth metal hydroxide as the base. The working-up and the double excess of hydroxyphenol are disadvantageous in this process. The reaction products obtained (monoether and some diether) must first be removed from the reaction mixture by extraction and must be isolated with the separation of large quantities of solvent. Thereafter, the unreacted hydroxyphenol and the solvent used for the alkylation can be obtained from the aqueous phase by means of a further distillation (two-phase working-up process).

The same problems and difficulties in the working-up process occur if, analogously to DOS No. 2,845,429, the reaction is carried out using alkali metal carbonates in dipolar aprotic solvents without, however, using the large excesses of pyrocatechol, as in DOS No. 2,452,936. In this process as well, an extensive reaction of pyrocatechol with a good mono-ether/diether ratio is not achieved. In addition, both processes are limited to reaction with the more reactive alkyl halides.

The present invention now provides a process for the preparation of a monoalkyl ether of hydroxyphenol, of the general formula

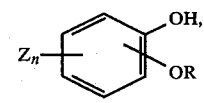

in which
Z represents hydrogen or a substituent which is stable under the reaction conditions,
R represents lower alkyl and
n represents 1, 2, 3 or 4, each Z being selected independently when n is 2 or more,
in which a hydroxyphenol of the general formula

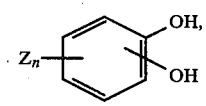

in which Z and n have the meanings given above, is reacted with an alkyl halide, alkyl sulphonate or aryl sulphonate of the general formula

         (III), in which
R represents lower alkyl and
X represents halogen, alkylsulphonyloxy or arylsulphonyloxy,
in the presence of an alkali metal base or alkaline earth metal base at a temperature of from 130° to 200° C., wherein the reaction is carried out in the presence of a polyhydroxyalkyl ether with at least one OH group.

Hydrogen, alkyl, halogen or nitro are preferred substituents Z in the formulae (I) and (II). Hydrogen is particularly preferred.

Pyrocatechol is a very particularly preferred compound of the formula (II).

Halogen, in particular chlorine, $C_{1-4}$-alkylsulphonyl, phenylsulphonyl or p-tolylsulphonyl are preferred substituents X in the formula (III).

It is particularly surprising that the hydroxyphenol ethers are obtained in high yields in relatively short reaction times by choosing polyhydroxyalkyl ethers with at least one free OH group as diluents. The high yields are achieved without addition of a co-catalyst. In spite of excess of alkylating agent, the formation of the corresponding diether is limited. A high to quantitative hydroxphenol conversion, with high selectivity of the monoether formation, is thus possible. The side-reactions due to nuclear alkylation are extremely limited.

The process according to the invention is distinguished by a particularly simple working-up process. After filtration of the salts formed, the organic phase obtained is subjected to a distillation process. In this process, not only is the solvent used recovered, but simultaneously, by means of further distillation, the isolation in highly pure form of the monether formed is achieved.

If pyrocatechol and isopropyl chloride are used as starting materials, the course of the reaction can be represented by the following equation:

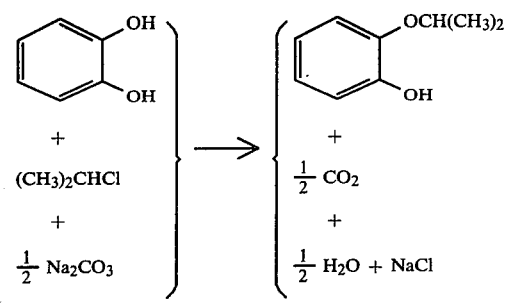

In carrying out the process according to the invention, 1 mol of hydroxyphenol is allowed to react with, in general, 1.2 to 2.0 mols of alkylating agent. The ratio 1.5 to 1.8 mols of alkylating agent per mol of hydroxyphenol is preferred. The diluent is generally employed in the ratio 1.0 to 4.0 parts by weight per part by weight of hydroxyphenol. The ratio 1.5 to 2.5 kg of diluent per kg of hydroxyphenol is convenient.

The reaction is carried out in the presence of a base. Alkali metal or alkaline earth metal hydroxides, carbonates or bicarbonates may be mentioned as examples of bases. Sodium carbonate or sodium bicarbonate and potassium carbonate or potassium bicarbonate are preferred. The alkali metal base is, in general, added in the ratio 1.0 to 2.0 base equivalents.

The reaction is generally carried out in a pressure reactor. It is advisable to carry out the reaction in the absence of air. The reaction pressure is primarily determined by the $CO_2$ liberated in the reaction and by the boiling point of the diluent or alkylating agent. The $CO_2$ formed can be continuously released at elevated pressure during the reaction.

The reaction is carried out at a temperature from about 130° to 200° C., preferably about 150° to 180° C.

The polyhydroxyalkyl ether having at least one free OH group, used as a diluent, is preferably selected from $C_{1-4}$-monoalkyl ethers of $C_{2-4}$-alkylene glycols; glycol monomethyl ether is particularly preferred.

The water formed in the reaction or carried over by the materials employed is removed in the working-up process by distillation of an azeotropic mixture. The salts formed during the reaction or excess base can be conveniently separated off subsequently to the reaction by means of filtration. The organic phase obtained yields, on distillation, the alkylating agent employed in excess, the water of reaction formed, in the form of an azeotropic mixture, the solvent employed, as the pure component, and the monoether formed, in high purity and yield. The quantities of alkylating agent and solvent recovered may be directly reused in the next cycle, without further purification. The product pyrocatechol mono-isopropyl ether is known and is used for the preparation of insecticidal plant protection agents.

The present invention is illustrated in and by the following examples:

EXAMPLE 1

896 g of pyrocatechol (8 mols), 1,157 g of isopropyl chloride, technical grade (14 mols), 1,613 g of glycol monomethyl ether and 638 g of sodium carbonate, technical grade (6 mols) were initially introduced into a 10 liter stainless steel reactor; the autoclave was flushed with $N_2$ and heated to 170° C., while stirring. The resulting pressure was continously released at 13 to 15 bars. After a reaction time of 6 hours, the reaction mixture was cooled to 20° C. and filtered off from the salt precipitate, the filtration residue was washed with twice 500 g of glycol monomethyl ether and the organic phase obtained was subjected to a distillation process. The excess isopropyl chloride was recovered in high purity as the first fraction under normal pressure at 35°–45° C. On further distillation, to 105° C. under normal pressure, an azeotropic mixture passed over, which contained the water of reaction formed, the by-products formed and a little glycol monomethyl ether. This fraction was most appropriately discarded.

The fraction to about 118° C. under normal pressure was, according to the conditions of distillation, relatively small and contained the remaining by-product methylglycol isopropyl ether, together with the solvent. The solvent was most appropriately distilled off at 20 mm Hg and at a boiling point above 40° C. 2,250 g of pure methylglycol, which together with the solvent content of the salt residue (100 g) yielded a recovery rate of 90%, were thereby obtained. The isopropoxyphenol formed was obtained in high purity with a yield of 81.4% as the fifth fraction at 108°–110° C. and at a pressure of 20 mm Hg. The distillation residue was discarded. The diether portion was 5% of theory according to gas chromatographic analysis.

EXAMPLE 2

56 g of pyrocatechol, technical grade (0.5 mol), 62 g of isopropyl chloride, technical grade (0.75 mol), 46.4 g of sodium carbonate, technical grade (0.44 mol) and 100 g of glycol monomethyl ether were initially introduced into a 0.7 liter stainless steel autoclave. The autoclave was flushed with $N_2$ and stirred for 5 hours at 170° C. The resulting pressure ($CO_2$) was continuously released at 15 bars. After the autoclave had been cooled and the pressure released, the salt precipitate was filtered off from the reaction mixture and the former was rinsed with twice 50 ml of solvent. The organic phase thus obtained contained the monoether in a yield of 76% of theory, according to gas chromatographic analysis; 3.4% of theory of diether were formed.

EXAMPLE 3

337 g of pyrocatechol, technical grade (3 mols), 372 g of isopropyl chloride, technical grade (4.5 mols), 245 g of sodium carbonate, technical grade (2.25 mols) and 557 g of glycol monomethyl ether were initially introduced into a 3 liter stainless steel autoclave. After the autoclave had been flushed with $N_2$, it was heated for 6 hours at 170° C. A maximum pressure of 29 bars was produced. After the autoclave had been cooled and the pressure released, the salt precipitate was filtered and washed twice with 200 ml of solvent. The preparative working-up analogously to Example 1 gave a yield of monoether of 77% of theory; the gas chromatographic analysis of the organic phase showed a yield of diether of 3%.

EXAMPLE 4

56 g of pyrocatechol, technical grade (0.5 mol), 73 g of isopropyl chloride, technical grade (0.87 mol), 40 g of sodium carbonate, technical grade (0.37 mol) and 100 g of glycol monomethyl ether were initially introduced into a 0.7 liter stainless steel autoclave, the autoclave was flushed with $N_2$ for a short time and the reaction mixture was stirred for 3 hours at 190° C. A pressure of 29 bars was established. After the autoclave had been cooled and the pressure released, the salt precipitate was filtered off and washed, and the organic phase was analyzed by gas chromatography. Under these conditions, the monoether was obtained in a yield of 79% of theory, with a diether portion of 3.7% of theory.

EXAMPLE 5

56 g of pyrocatechol, technical grade (0.5 mol), 73 g of isopropyl chloride, technical grade (0.87 mol), 46 g of sodium carbonate, technical grade (0.43 mol) and 150 g of glycol monomethyl ether were stirred for 3 hours at 190° C. in a 0.7 liter stainless steel autoclave. After filtration of the salts, the organic phase contained the monoether in a yield of 80%, relative to pyrocatechol employed; 4% of diether were formed (gas chromatographic analysis).

EXAMPLE 6

896 g of pyrocatechol, technical grade (8 mols), 992 g of isopropyl chloride, technical grade (12 mols), 1,485 g of glycol monomethyl ether and 828 g of potassium carbonate, technical grade (6 mols) were initially introduced into a 10 liter stainless steel reactor. After the autoclave had been flushed with $N_2$, it was heated to 170° C., while stirring. During the reaction time of 6 hours, the resulting pressure was continuously released at 15 bars. After the autoclave had been cooled, the reaction mixture was worked up analogously to Example 1. Excess isopropyl chloride was no longer found. The yield of isopropoxyphenol was 77%; the diether formation was 12% of theory, according to gas chromatographic analysis of the organic phase.

EXAMPLE 7

896 g of pyrocatechol, technical grade (8 mols), 1,157 g of isopropyl chloride, technical grade (14 mols), 1,610 g of glycol monomethyl ether and 828 g of $K_2CO_3$ (6 mols) were initially introduced into a 10 liter stainless steel autoclave. The autoclave was first flushed with $N_2$ and then stirred for 6 hours at 150° C. A maximum pressure of 22 bars was established. After the autoclave had been cooled, the reaction mixture was worked up analogously to Example 1. 215 g of isopropyl chloride (91.6% of the starting material) were obtained as a first fraction; the isopropoxyphenol was obtained as the fifth fraction in a yield of 80.3%; the diether was produced with a yield of 8.2%, according to gas chromatographic analysis of the organic phase.

EXAMPLE 8

When the reaction was carried out analogously to Example 7, but for 6 hours at 170° C., a maximum pressure of 28 bars was established. After the autoclave had been cooled and the reaction mixture worked up analogously to Example 1, 111 g of isopropyl chloride (10% of the starting material) were recovered firstly as a first fraction. The isopropoxyphenol formed was produced as the fifth fraction with high purity in a yield of 85% of theory; the diether portion (according to gas chromatography of the organic phase) was 9.6% of theory.

EXAMPLE 9

When the reaction was carried out analogously to Example 8, but the $CO_2$ formed was released continuously at approximately 16 bars, the following distribution of products was found after distillation of the organic phase: the portion of unreacted isopropyl chloride was 4.1% of starting material; the yield of isopropoxyphenol was 86% of theory, according to gas chromatography of the organic phase.

EXAMPLE 10

18.45 kg (168 mols) of pyrocatechol (technical grade) and 18.65 kg (125 mols) of anhydrous sodium carbonate were initially introduced into a stainless steel autoclave of 100 liter capacity, the autoclave was flushed with nitrogen and after addition of 36.9 kg of glycol monomethyl ether the mixture was stirred to suspension. Thereafter, the suspension was heated to 170° C., while stirring. Carbon dioxide was already liberated and an internal boiler pressure of approximately 14 bars built up. Thereafter, 26.32 kg (335 mols) of isopropyl chloride (technical grade, distilled) were pumped into the autoclave during the course of 1 hour at an internal boiler temperature of 170° C. During this operation, the internal boiler pressure was kept at 15 bars (absolute) by partial release of pressure. After the total reaction time of 10 hours, the boiler content was cooled to 20° C. and the pressure released. The solid material was filtered off by means of a suction filter. The filtration residue was washed with four times 6 kg of glycol monomethyl ether. Filtrate and washings were combined and separated by means of discontinuous distillation in a rectifying column (height 8 m, nominal width 200 mm, charge glass Raschig rings 15 mm diameter, column made of glass). The distillation was carried out as described under Example 1. The yield of isopropoxyphenol in the fifth fraction was 82% of theory.

It will be appreciated that the instant specification and examples are set forth by way of illustration and not limitation, and that various modifications and changes may be made without departing from the spirit and scope of the present invention.

We claim:
1. A process for the preparation of a monoalkyl ether of a hydroxyphenol of the formula

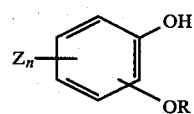

in which
  Z each independently is hydrogen or a substituent which is stable under the reaction conditions,
  R is lower alkyl, and
  n is 1, 2, 3 or 4,
comprising reacting a hydroxyphenol of the formula

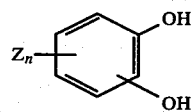

with an alkyl halide, alkyl sulphonate or aryl sulphonate alkylating agent of the formula

R—X in which X is a halogen atom, or an alkylsulphonyloxy or arylsulphonyloxy radical, at a temperature from about 150° C. to 200° C. and in the presence of an alkali metal base or alkaline earth metal base and of a diluent comprising a mono-alkyl ether of an alkylene glycol.

2. A process according to claim 1, wherein about 1.2 to 2 mols of alkylating agent are employed per mole of hydroxyphenol.

3. A process according to claim 1, wherein about 1 to 2 mols of the base equivalent are employed per mol of hydroxyphenol.

4. A process according to claim 1, wherein about 1 to 4 parts by weight of the mono-alkyl ether of an alkylene glycol per part of hydroxyphenol are employed as diluent.

5. A process according to claim 1, wherein Z each independently is hydrogen, alkyl, hydrogen or nitro.

6. A process according to claim 1, wherein the hydroxyphenol is pyrocatechol.

7. A process according to claim 1, wherein X is chlorine, $C_{1-4}$-alkylsulphonyl, phenylsulphonyl or tolylsulphonyl.

8. A process according to claim 1, wherein the alkylating agent R is isopropyl.

9. A process according to claim 1, wherein the monoalkyl ether of an alkylene glycol is a lower alkylene glycol mono-$C_{1-4}$-alkyl ether.

10. A process according to claim 1, wherein the monoalkyl ether of an alkylene glycol is glycol monomethyl ether.

11. A process according to claim 1, wherein the base is an alkali metal carbonate or an alkali metal bicarbonate.

12. A process according to claim 1, wherein the base is sodium carbonate, sodium bicarbonate, potassium carbonate or potassium bicarbonate.

13. A process according to claim 12, wherein the hydroxyphenol is pyrocatechol, the alkylating agent is isopropyl chloride, isopropyl $C_{1-4}$-alkyl-1-sulphonate, isopropyl benzenesulphonate or isopropyl toluenesulphonate, and the mono-alkyl ether of an alkylene glycol is glycol monomethyl ether, about 1.5 to 1.8 mols of alkylating agent and about 1 to 2 mols of the base being employed per mol of pyrocatechol, about 1.5 to 2.5 parts by weight of the glycol monomethyl ether being employed per part by weight of pyrocatechol, the reaction being effected in an inert atmosphere under elevated pressure.

* * * * *